United States Patent [19]
Berg

[11] Patent Number: 5,776,322
[45] Date of Patent: Jul. 7, 1998

[54] SEPARATION OF 4-METHYL-2-PENTANOL FROM 3-METHYL-1-BUTANOL BY AZEOTROPIC DISTILLATION

[76] Inventor: Lloyd Berg, 1314 S. 3rd Ave., Bozeman, Mont. 59715

[21] Appl. No.: 859,436

[22] Filed: May 20, 1997

[51] Int. Cl.[6] .............................. B01D 3/36; C07C 29/84
[52] U.S. Cl. ...................... 203/57; 203/60; 203/68; 203/69; 203/70; 568/913
[58] Field of Search ...................... 203/57, 69, 68, 203/70, 60; 568/913

[56] References Cited

U.S. PATENT DOCUMENTS

| | | | |
|---|---|---|---|
| 2,483,246 | 9/1949 | Stribley | 203/60 |
| 2,500,329 | 3/1950 | Steitz | 203/69 |
| 4,204,915 | 5/1980 | Karata et al. | 203/69 |
| 5,338,410 | 8/1994 | Berg | 203/60 |
| 5,437,770 | 8/1995 | Berg | 203/57 |
| 5,447,608 | 9/1995 | Berg | 203/69 |
| 5,645,695 | 7/1997 | Berg | 203/70 |
| 5,658,435 | 8/1997 | Berg | 568/913 |

FOREIGN PATENT DOCUMENTS

| | | | |
|---|---|---|---|
| 0216634 | 12/1984 | Germany | 203/60 |
| 0967471 | 8/1964 | United Kingdom | 203/60 |

*Primary Examiner*—Virginia Manoharan

[57] ABSTRACT

4-Methyl-2-pentanol cannot be separated from 3-methyl-1-butanol by distillation because of the closeness of their boiling points. 4-Methyl-2-pentanol can be easily separated from 3-methyl-1-butanol by azeotropic distillation. Effective agents are m-xylene and cumene.

2 Claims, No Drawings

SEPARATION OF 4-METHYL-2-PENTANOL FROM 3-METHYL-1-BUTANOL BY AZEOTROPIC DISTILLATION

FIELD OF THE INVENTION

This invention relates to a method for separating 4-methyl-2-pentanol from 3-methyl-1-butanol using certain organic compounds as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

4-Methyl-2-pentanol and 3-methyl-1-butanol boil only two degrees apart and have a relative volatility of 1.1 and are difficult to separate by conventional rectification. Table 2 shows that to get 99% purity, 12 actual plates are required. With an agent giving a relative volatility of 1.4, only 38 actual plates are required.

TABLE 2

Theoretical and Actual Plates Required vs. Relative Volatility for 4-Methyl-2-pentanol - 3-Methyl-1-butanol Separation

| Relative Volatility | Theoretical Plates Required At Total Reflux, 99 Purity | Actual Plates Required, 75% Eff. |
|---|---|---|
| 1.1 | 95 | 127 |
| 1.3 | 34 | 46 |
| 1.4 | 26 | 35 |

OBJECTIVE OF THE INVENTION

The object of this invention is to provide processes or methods of azeotropic distillation that will enhance the relative volatility of 4-methyl-2-pentanol to 3-methyl-1-butanol in their separation in a rectification column. It is a further object of this invention to identify effective azeotropic distillation agents that are stable and can be recycled.

SUMMARY OF THE INVENTION

The objects of this invention are provided by processes for the separation of 4-methyl-2-pentanol from 3-methyl-1-butanol which entails the use of certain organic compounds when employed as the agent in azeotropic distillation.

TABLE 3

Effective Azeotropic Distillation Agents For Separating 4-Methyl-2-pentanol From 3-Methyl-1-butanol

| Compounds | Relative Volatility 3-Methyl-1-butanol/4-Methyl-2-pentanol |
|---|---|
| None | 1.1 |
| p-Xylene | 1.35 |
| m-Xylene | 1.4 |
| o-Xylene | 1.25 |
| Ethyl benzene | 1.35 |
| Octane | 1.25 |
| Toluene | 1.3 |
| n-Nonane | 1.25 |
| Cumene | 1.35* |
| 1-Octene | 1.25 |
| 2,2,4-Trimethyl pentane | 1.35 |
| Dimethyl carbonate | 1.35 |

*Reverses the alcohols 4-Methyl-2-pentanol/3-Methyl-1-butanol

DETAILED DESCRIPTION OF THE INVENTION

I have discovered that certain organic compounds will effectively increase the relative volatility between 4-methyl-2-pentanol and 3-methyl-1-butanol during rectification when employed as the agent in azeotropic distillation. Table 3 summarizes the data obtained with these agents. The agents which are effective in azeotropic distillation (Table 3) are p-xylene, m-xylene, o-xylene, ethyl benzene, octane, toluene, n-nonane, cumene, 2,2,4-trimethyl pentane, 1-octene and dimethyl carbonate.

THE USEFULNESS OF THE INVENTION

The usefulness or utility of this invention can be demonstrated by referring to the data presented in Tables 1, 2 and 3. All of the successful agents show that 4-methyl-2-pentanol can be separated from 3-methyl-1-butanol by means of azeotropic distillation and that the ease of separation is considerable.

WORKING EXAMPLES

EXAMPLE 1

Fifty grams of 4-methyl-2-pentanol—3-methyl-1-butanol mixture and 50 grams of m-xylene as the azeotrope forming agent were charged to a vapor-liquid equilibrium still and refluxed for two hours. The vapor composition was 69.2% 4-methyl-2-pentanol, 30.8% 3-methyl-1-butanol; the liquid composition was 76% 4-methyl-2-pentanol, 24% 3-methyl-1-butanol. This is a relative volatility of 4-methyl-2-pentanol to 3-methyl-1-butanol of 1.4.

EXAMPLE 2

Fifty grams of 4-methyl-2-pentanol—3-methyl-1-butanol mixture and 50 grams of cumene as the azeotrope forming agent were charged to a vapor-liquid equilibrium still and refluxed for three hours. The vapor composition was 13.2% 4-methyl-2-pentanol, 86.8% 3-methyl-1-butanol; the liquid composition was 10.1% 4-methyl-2-pentanol, 89.9% 3-methyl-1-butanol. This is a relative volatility of 3-methyl-1-butanol to 4-methyl-2-pentanol of 1.35.

I claim:

1. A method for recovering 3-methyl-1-butanol from a mixture of 3-methyl-1-butanol and 4-methyl-2-pentanol which consists essentially of distilling a mixture consisting of 3-methyl-1-butanol and 4-methyl-2-pentanol in the presence of an azeotrope forming agent, recovering the 3-methyl-1-butanol and the azeotrope forming agent as overhead product and obtaining the 4-methyl-2-pentanol as bottoms product, wherein said azeotrope forming agent is one material selected from the group consisting of p-xylene, m-xylene, o-xylene, ethyl benzene, octane, toluene, n-nonane, 1-octene, 2,2,4-trimethyl pentane and dimethyl carbonate.

2. A method for recovering 4-methyl-2-pentanol from a mixture of 4-methyl-2-pentanol and 3-methyl-1-butanol which consists essentially of distilling a mixture consisting of 4-methyl-2-pentanol and 3-methyl-1-butanol in the presence of an azeotrope forming agent, recovering the 4-methyl-2-pentanol and the azeotrope forming agent as overhead product and obtaining the 3-methyl-1-butanol as bottoms product, wherein said azeotrope forming agent consists of cumene.

* * * * *